United States Patent
Takada et al.

(10) Patent No.: US 11,135,137 B2
(45) Date of Patent: Oct. 5, 2021

(54) DENTAL PHOTOPOLYMERIZABLE COMPOSITION

(71) Applicant: GC Corporation, Shizuoka (JP)

(72) Inventors: Daisuke Takada, Tokyo (JP); Shuji Kariya, Tokyo (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 16/643,978

(22) PCT Filed: May 14, 2018

(86) PCT No.: PCT/JP2018/018546
§ 371 (c)(1),
(2) Date: Mar. 3, 2020

(87) PCT Pub. No.: WO2019/049426
PCT Pub. Date: Mar. 14, 2019

(65) Prior Publication Data
US 2021/0038481 A1    Feb. 11, 2021

(30) Foreign Application Priority Data
Sep. 7, 2017 (JP) .............................. JP2017-171877

(51) Int. Cl.
*C08F 2/46* (2006.01)
*C08F 2/50* (2006.01)
*C08G 61/04* (2006.01)
*A61K 6/887* (2020.01)
*A61K 6/76* (2020.01)
*A61K 6/62* (2020.01)
*A61C 13/00* (2006.01)

(52) U.S. Cl.
CPC ............... *A61K 6/887* (2020.01); *A61K 6/62* (2020.01); *A61K 6/76* (2020.01); *A61C 13/0019* (2013.01)

(58) Field of Classification Search
CPC . A61K 6/887; A61K 6/60; A61K 6/62; A61K 6/76; A61K 6/78; B33Y 80/00; B33Y 70/00; A61C 13/004; A61C 13/34; A61C 13/0019; C08L 33/08; C08L 33/10
USPC ........... 522/39, 33, 6, 71, 189, 184, 1; 520/1
See application file for complete search history.

(56) References Cited

U.S. PATENT DOCUMENTS

| | | | |
|---|---|---|---|
| 10,918,578 B2 * | 2/2021 | Murata | A61K 6/16 |
| 2009/0148813 A1 | 6/2009 | Sun et al. | |
| 2014/0131908 A1 | 5/2014 | Sun et al. | |
| 2018/0171052 A1 * | 6/2018 | Bonderer | C08K 3/22 |
| 2019/0163060 A1 * | 5/2019 | Skamser | G03F 7/031 |
| 2019/0254936 A1 * | 8/2019 | Suzuki | C08K 3/014 |
| 2020/0332046 A1 * | 10/2020 | Abuelyaman | B33Y 80/00 |

FOREIGN PATENT DOCUMENTS

| | | | | |
|---|---|---|---|---|
| JP | 2014-015408 | | 1/2014 | |
| JP | 2014015408 | * | 1/2014 | |
| JP | 2016-007392 | | 1/2016 | |
| JP | 2016-505525 | | 2/2016 | |
| WO | WO-2018005501 A1 | * | 1/2018 | G03F 7/031 |

OTHER PUBLICATIONS

Akizumi et al, JP 2014015408 Machine Translation, Jan. 30, 2014 (Year: 2014).*
Akitsumi et al, JP 201415408 Machine Translation, Jan. 30, 2014 (Year: 2014).*
International Search Report for PCT/JP2018/018546 dated Jun. 19, 2018.

* cited by examiner

*Primary Examiner* — Jessica Whiteley
(74) *Attorney, Agent, or Firm* — IPUSA, PLLC

(57) ABSTRACT

According to one aspect of the present invention, a dental photopolymerizable composition includes: a (meth)acrylate compound; a filler; a photopolymerization initiator; and a phthalic acid derivative and/or a thiophene derivative, wherein a content of the phthalic acid derivative and/or the thiophene derivative is greater than or equal to 0.05% by mass and less than or equal to 0.25% by mass.

6 Claims, No Drawings

DENTAL PHOTOPOLYMERIZABLE COMPOSITION

TECHNICAL FIELD

The present invention relates to a dental photopolymerizable composition.

BACKGROUND ART

In recent years, three-dimensional fabrication (Additive manufacturing) techniques are being developed, and the three-dimensionally fabricated dental prostheses accuracy is higher than that of a conventional one, in the dental field.

Accordingly, a photopolymerizable composition that is used in the three-dimensional fabrication of dental prostheses is developed (see, for example, Patent Document 1).

PRIOR ART DOCUMENTS

Patent Documents

[Patent Document 1] Japanese National Publication of International Patent Application No. 2016-505525

DISCLOSURE OF THE INVENTION

Problem to be Solved by the Invention

However, it is desirable to further enhance the accuracy of three-dimensional fabrication of dental prostheses.

Accordingly, it is an object of one aspect of the present invention to provide a dental photopolymerizable composition that can enhance the accuracy of three-dimensional fabrication of a dental prosthesis.

Means for Solving the Problem

According to one aspect of the present invention, a dental photopolymerizable composition includes: a (meth)acrylate compound; a filler; a photopolymerization initiator; and a phthalic acid derivative and/or a thiophene derivative, wherein a content of the phthalic acid derivative and/or the thiophene derivative is greater than or equal to 0.05% by mass and less than or equal to 0.25% by mass.

Effects of the Invention

According to one aspect of the present invention, it is possible to provide a dental photopolymerizable composition that can enhance the accuracy of three-dimensional fabrication of a dental prosthesis.

EMBODIMENT FOR CARRYING OUT THE INVENTION

Next, embodiments for carrying out the present invention will be described.

The dental photopolymerizable composition according to the present embodiment includes a (meth)acrylate compound, a filler, a photopolymerization initiator, a phthalic acid derivative and/or a thiophene derivative.

The phthalic acid derivative is preferably a phthalate ester, and is more preferably a compound that is represented by the following general formula.

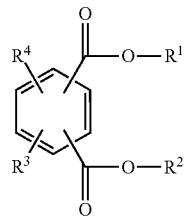

(In the formula, $R^1$ and $R^2$ are each independently an alkyl group, $R^3$ is a hydrogen atom, an amino group, or a hydroxyl group, and $R^4$ is an amino group or a hydroxyl group.)

Examples of alkyl groups at $R^1$ and $R^2$ include a methyl group, an ethyl group, an n-propyl group, an isopropyl group, and the like. Among these, an alkyl group having 1 to 3 carbon atoms is preferable, and an alkyl group having 1 to 2 carbon atoms is more preferable.

Examples of the phthalate ester include dimethyl-2,5-dihydroxy terephthalate, diethyl-2,5-dihydroxy terephthalate, dimethylamino terephthalate, diethylamino terephthalate, and the like.

Examples of phthalic acid derivatives other than phthalate esters include o-phthaldehyde and the like.

Note that a phthalic acid derivative may be used alone or two or more kinds of phthalic acid derivatives may be used in combination.

The thiophene derivative is preferably a thiophene having a benzoxazol-2-yl group and is more preferably a thiophene in which the 2- and 5-positions are substituted with a benzoxazol-2-yl group.

Note that the benzoxazol-2-yl group may be substituted with an alkyl group.

Examples of the thiophene derivative include 2,5-bis(5-tert-butyl-2-benzoxazolyl)thiophene, 2,5-bis(6,6'-bis(tert-butyl)-benzoxazol-2-yl)thiophene, and the like.

Note that a thiophene derivative may be used alone or two or more kinds of thiophene derivatives may be used in combination.

The content of the phthalic acid derivative and/or the thiophene derivative in the dental photopolymerizable composition according to the present embodiment is greater than or equal to 0.05% by mass and less than or equal to 0.25% by mass, and is preferably greater than or equal to 0.09% by mass and less than or equal to 0.21% by mass. When the content of the phthalic acid derivative and/or the thiophene derivative in the dental photopolymerizable composition is less than 0.05% by mass, the accuracy of three-dimensional fabrication of a dental prosthesis is lower. When the content of the phthalic acid derivative and/or the thiophene derivative in the dental photopolymerizable composition exceeds 0.25% by mass, it is impossible to fabricate a dental prosthesis three-dimensionally or a part of fabricated dental prosthesis is delaminated.

As the (meth)acrylate compound, a compound such as monomers, oligomers, or prepolymers having a methacryloyloxy group and/or an acryloyloxy group can be used.

Examples of monomers having a methacryloyloxy group and/or an acryloyloxy group include methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-ethoxyethyl (meth)acrylate, 2-methoxyethyl (meth)acrylate, 2-ethylhexyl (meth)acrylate, benzyl (meth)acrylate, 2-hydroxy-1,3-di (meth)acryloyloxypropane, ethylene glycol di (meth)acrylate, diethylene glycol di (meth)acrylate, triethylene glycol di (meth)acrylate, butylene glycol di (meth)acrylate, neopentyl glycol di (meth)acrylate, 1,3-butanediol di (meth)acrylate, 1,4-butanediol di (meth)acrylate, 1,6-hexanediol di (meth)acrylate, trimethylolpropane tri (meth)acrylate, trimethylolethane tri (meth)acrylate, pentaerythritol tri (meth)acrylate, trimethylol methane tri (meth)acrylate, pentaerythritol tetra (meth)acrylate, polybutylene glycol di (meth)acrylate, ethoxylated bisphenol A di (meth)acrylate, bisphenol A diglycidyl (meth)acrylate, and the like.

Also, a (meth)acrylate having a urethane bond may be used as a (meth)acrylate compound other than above.

Examples of the (meth)acrylate having a urethane bond include di-2-(meth)acryloyloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H) triazine-2,4,6-trione, and the like.

Examples that are used as the (meth)acrylate having a urethane bond other than above include a (meth)acrylate of a urethane oligomer obtained by reacting 2,2'-bis(4-hydroxycyclohexyl)propane with 2-oxypanone, hexamethylene diisocyanate, and 2-hydroxyethyl (meth)acrylate, and a (meth)acrylate of a urethane oligomer obtained by reacting 1,3-butanediol with hexamethylene diisocyanate, and 2-hydroxyethyl (meth)acrylate.

Note that a (meth)acrylate compound may be used alone or two or more kinds of (meth)acrylate compounds may be used in combination.

The content of the (meth)acrylate compound in the dental photopolymerizable composition according to the present embodiment is preferably greater than or equal to 35% by mass and less than or equal to 99% by mass, and is more preferably greater than or equal to 60% by mass and less than or equal to 95% by mass.

Examples of the material constituting the filler include glasses such as silica glass, barium glass, alumina glass, potassium glass, fluoroaluminosilicate glass, and oxide such as synthetic zeolite, calcium phosphate, feldspar, silica, aluminum silicate, calcium silicate, magnesium carbonate, hydrous silicate, hydrous calcium silicate, hydrous aluminum silicate, quartz, aluminum oxide, zirconium oxide, magnesium oxide, titanium oxide, barium oxide, strontium oxide, and yttrium oxide, and the like.

Here, instead of the filler described above or together with the filler described above, it is possible to use an organic/inorganic composite filler prepared by mixing the filler described above with a (meth)acrylate compound in advance and then pulverizing it.

Note that a filler may be used alone or two or more kinds of fillers may be used in combination.

The median diameter of the filler is preferably greater than or equal to 1 nm and less than or equal to 10 μm, and is more preferably greater than or equal to 10 nm and less than or equal to 5 μm. At this time, a filler having a median diameter greater than or equal to 1 nm and less than or equal to 100 nm may be used together with a filler having a median diameter greater than or equal to 1 μm and less than or equal to 10 μm.

Note that the median diameter of the filler means, in the particle size distribution based on number that is obtained by a laser diffraction/scattering method, a particle diameter at which the integrated value is 50%.

Note that the filler may be subjected to a hydrophobic treatment with a silane coupling agent.

Examples of the silane coupling agent include γ-methacryloyloxypropyltrimethoxysilane, inyltrichlorosilane, vinyltriethoxysilane, vinyltrimethoxysilane, vinyltriacetoxysilane, vinyltris (2-methoxyethoxy) silane, 8-methacryloyloxyoctyltrimethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, 11-methacryloyloxyundecyltrichlorosilane, 11-methacryloyloxyundecyldimethoxymethylsilane, 12-methacryloyloxidedecyltrimethoxysilane, 13-methacryloyloxytridecyltrimethoxysilane, dimethyldichlorosilane, hexamethyldisilazane, and the like.

The content of the filler in the dental photopolymerizable composition according to the present embodiment is preferably greater than or equal to 0.1% by mass and less than or equal to 75% by mass, and is more preferably greater than or equal to 1% by mass and less than or equal to 40% by mass.

Examples of the photopolymerization initiator include camphorquinone, benzyl, diacetyl, benzyl dimethyl ketal, benzyl diethyl ketal, benzyl bis(2-methoxyethyl) ketal, 4,4'-dimethylbenzyl-dimethylketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxantone, 2,4-diethylthioxanthone, 2,4-diisopropylthioxanthonton 2-chloro-7-trifluoromethylthioxanthone, thioxanthone-10, 10-dioxide, thioxanthone-10-oxide, benzoin methyl ether, benzoin ethyl ether, benzoin isopropyl ether, benzoin isobutyl ether, benzophenone, bis(4-dimethylaminophenyl) ketone, 4,4'-bisdiethylaminobenzophenone, 2,4,6-trimethylbenzoyldiphenylphosphine oxide, bis(2,4,6-trimethylbenzoyl)-phenylphosphine oxide, and the like, and two or more kinds of these may be used in combination.

The content of the photopolymerization initiator in the dental photopolymerizable composition according to the present embodiment is preferably greater than or equal to 0.01% by mass and less than or equal to 10% by mass, and is more preferably greater than or equal to 0.05% and less than or equal to 5% by mass.

The dental photopolymerizable composition according to the present embodiment may further include, as needed, a photopolymerization accelerator, a polymerization inhibitor, a pigment, a preservative stabilizer, and the like.

Examples of the photopolymerization accelerator include tertiary amines such as N,N-dimethyl-p-toluidine, N,N-dimethylaminoethylmethacrylate, triethanolamine, methyl 4-dimethylaminobenzoate, ethyl 4-dimethylaminobenzoate, isoamyl 4-dimethylaminobenzoate, and the like, and two or more kinds of these may be used in combination.

The content of the photopolymerization accelerator in the dental photopolymerizable composition according to the present embodiment is preferably greater than or equal to 0.01% by mass and less than or equal to 10% by mass, and is more preferably greater than or equal to 0.1% by mass and less than or equal to 5% by mass.

Examples of the polymerization inhibitor include 2,6-di-tert-butyl-p-cresol, hydroquinone, dibutylhydroquinone, dibutylhydroquinone monomethyl ether, hydroquinone monomethyl ether, 2,6-di-t-butylphenol, and the like, and two or more kinds of these may be used in combination.

The content of the polymerization inhibitor in the dental photopolymerizable composition according to the present embodiment is preferably greater than or equal to 0.001% by mass and less than or equal to 5% by mass, and is more preferably greater than or equal to 0.05% by mass and less than or equal to 2% by mass.

Examples of the pigment include titanium dioxide (white), iron oxide (yellow, red), triferric oxide (black), and the like, and two or more kinds of these may be used in combination.

The content of the pigment in the dental photopolymerizable composition according to the present embodiment is preferably greater than or equal to 0.001% by mass and less than or equal to 1% by mass, and is more preferably greater than or equal to 0.05% by mass and less than or equal to 0.5% by mass.

Examples of the preservative stabilizer include 2-(2-hydroxy-5-methylphenyl)-2H-benzotriazole and the like.

The content of the preservative stabilizer in the dental photopolymerizable composition according to the present embodiment is preferably greater than or equal to 0.01% by mass and less than or equal to 2% by mass, and is more preferably greater than or equal to 0.05% by mass and less than or equal to 1% by mass.

The dental photopolymerizable composition according to the present embodiment can be applied to three-dimensional fabrication of dental prostheses, and can also be applied to three-dimensional fabrication of dental models or the like.

Examples of the dental prostheses include inlays, crowns, bridges, dentures, upper structures of implants, and the like.

EXAMPLES

In the following, although Examples of the present invention will be described, the present invention is not limited to Examples.

Examples 1-4 and Comparative Examples 1-3

The respective components were mixed at proportions indicated in Table 1 [Part by Mass] to prepare photopolymerizable compositions.

<Three-Dimensional Fabrication of Full Bridge>

After preparing an intraoral gypsum model, the gypsum model was scanned with an optical scanner to create digital data (model). Next, after using CAD to design a full bridge (dental prosthesis) conforming to the digital data, a 3D printer and the dental photopolymerizable composition were used to three-dimensionally fabricate a full bridge.

The surface property and the accuracy of the three-dimensional fabricated bridge were then evaluated.

<Surface Property>

The full bridge was visually checked to evaluate the surface property. Note that the determination criteria for the surface property are as follows.

"Good": When the full bridge is successfully fabricated three-dimensionally

"Bad": When the three-dimensionally fabricated full bridge is delaminated

"Very bad": When the full bridge is not fabricated three-dimensionally

<Accuracy of Three-Dimensional Fabrication>

The full bridge was fitted to a gypsum model to evaluate the accuracy of the three-dimensional fabrication. Note that the determination criteria for the accuracy of three-dimensional fabrication are as follows.

"Good": When the full bridge fits the gypsum model

"Bad": When the full bridge does not fit the gypsum model

Table 1 indicates the evaluation results of the surface property and the accuracy of three-dimensional fabrication the full bridges.

TABLE 1

|  |  | Example 1 | Example 2 | Example 3 | Example 4 | Comparative Example 1 | Comparative Example 2 | Comparative Example 3 |
|---|---|---|---|---|---|---|---|---|
| PHTHALIC ACID DERIVATIVE | DIETHYL-2,5-DIHYDROXY TEREPHTHALATE | 0.1 | 0.2 | 0.25 |  |  | 0.5 | 0.3 |
| THIOPHENE DERIVATIVE | 2,5-BIS(5-TERT-BUTYL-2-BENZOXAZOLYL)THIOPHENE |  |  |  | 0.2 |  |  |  |
| (METH)ACRYLATE COMPOUND | DI-2-METHACRYLOYLOXYETHYL-2,2,4-TRIMETHYLHEXAMETHYLENE DICARBAMATE | 55 | 45 | 40 | 50 | 55 | 45 | 40 |
|  | ETHOXYLATED BISPHENOL A DI METHACRYLATE | 5 | 10 | 20 | 5 | 5 | 10 | 20 |
|  | TRIETHYLENE GLYCOL DI METHACRYLATE | 15 | 20 | 20 | 20 | 15 | 20 | 20 |
| FILLER | SILICA FILLER (MEDIAN DIAMETER: 1 μm) | 20 | 19 | 12 | 16 | 20 | 19 | 12 |
|  | SILICA FILLER (MEDIAN DIAMETER: 50 nm) | 2 | 3 | 5 | 6 | 2 | 3 | 5 |
| PHOTOPOLYMERIZATION INITIATOR | 2,4,6-TRIMETHYLBENZOYL-DIPHENYL-PHOSPHINE OXIDE | 2.2 | 2.2 | 2.2 | 2.2 | 2.2 | 2.2 | 2.2 |
| PHOTOPOLYMERIZATION ACCELERATOR | ETHYL 4-DIMETHYLAMINOBENZOATE | 0.6 | 0.6 | 0.6 | 0.6 | 0.6 | 0.6 | 0.6 |
| POLYMERIZATION INHIBITOR | 2,6-DI-TERT-BUTYL-P-CRESOL | 0.1 | 0.1 | 0.1 | 0.1 | 0.1 | 0.1 | 0.1 |
| PIGMENT | TITANIUM DIOXIDE | 0.07 | 0.07 | 0.07 | 0.07 | 0.07 | 0.07 | 0.07 |
|  | IRON OXIDE | 0.02 | 0.01 | 0.01 | 0.01 | 0.01 | 0.01 | 0.01 |
|  | TRIIRON TETROXIDE | 0.001 | 0.001 | 0.001 | 0.001 | 0.001 | 0.001 | 0.001 |
| SURFACE PROPERTY |  | GOOD | GOOD | GOOD | GOOD | GOOD | VERY BAD | BAD |
| ACCURACY OF THREE-DIMENSIONAL FABRICATION |  | GOOD | GOOD | GOOD | GOOD | BAD | — | GOOD |

Table 1 indicates that the accuracy of three-dimensional fabrication of the full bridges of the photopolymerizable compositions of Examples 1-4 is high.

In contrast, because the photopolymerizable composition of Comparative Example 1 does not contain a phthalic acid derivative or a thiophene derivative, the accuracy of three-dimensional fabrication of the full bridge is low.

In the photopolymerizable composition of Comparative Example 2, because the content of diethyl-2,5-dihydroxy terephthalate is 0.5% by mass, a full bridge cannot be three-dimensionally fabricated.

In the photopolymerizable composition of Comparative Example 3, because the content of diethyl-2,5-dihydroxy terephthalate is 0.3% by mass, part of the full bridge is delaminated.

The present international application is based upon and claims priority to Japanese Patent Application No. 2017-171877, filed on Sep. 7, 2017, the entire contents of Japanese Patent Application No. 2017-171877 are hereby incorporated herein by reference.

The invention claimed is:

1. A dental photopolymerizable composition comprising:
a (meth)acrylate compound;
a filler, wherein the total content of the filler is greater than or equal to 1% by mass and less than or equal to 40% by mass;
a photopolymerization initiator; and
a phthalic acid derivative and/or a thiophene derivative, wherein a total content of the phthalic acid derivative and/or the thiophene derivative is greater than or equal to 0.05% by mass and less than or equal to 0.25% by mass.

2. The dental photopolymerizable composition according to claim 1, wherein the dental photopolymerizable composition is used for three-dimensional fabrication of a dental prosthesis.

3. The dental photopolymerizable composition according to claim 1, wherein a content of the (meth)acrylate compound in the dental photopolymerizable composition is greater than or equal to 60% by mass and less than or equal to 95% by mass.

4. The dental photopolymerizable composition according to claim 1, wherein the filler includes a filler having a median diameter greater than or equal to 1 nm and less than or equal to 100 nm and a filler having a median diameter greater than or equal to 1 μm and less than or equal to 10 μm.

5. The dental photopolymerizable composition according to claim 1, wherein the phthalic acid derivative and/or the thiophene derivative is limited to a phthalic acid derivative.

6. The dental photopolymerizable composition according to claim 1, wherein the total content of the phthalic acid derivative and/or the thiophene derivative is greater than or equal to 0.09% by mass and less than or equal to 0.25% by mass.

* * * * *